US006134830A

United States Patent [19]
Welty

[11] Patent Number: 6,134,830
[45] Date of Patent: Oct. 24, 2000

[54] METHOD FOR STORING AND IMPROVING THE SURVIVAL RATE OF CONIFER SOMATIC EMBRYO GERMINANTS

[75] Inventor: Dorothy Elaine Welty, Tacoma, Wash.

[73] Assignee: Weyerhaeuser Company, Federal Way, Wash.

[21] Appl. No.: 09/174,496

[22] Filed: Oct. 16, 1998

Related U.S. Application Data

[60] Provisional application No. 60/066,897, Nov. 20, 1997.

[51] Int. Cl.[7] .............................. C12N 5/04; A01H 4/00; A01H 7/00; A01G 1/00; A01C 1/06
[52] U.S. Cl. .......................... 47/58.1; 435/420; 435/422; 435/430.1; 47/57.6
[58] Field of Search ................................... 47/58.1, 57.6; 435/420, 430.1, 422

[56] References Cited

U.S. PATENT DOCUMENTS

| | | | |
|---|---|---|---|
| 5,034,326 | 7/1991 | Pullman et al. | 435/240.4 |
| 5,036,007 | 7/1991 | Gupta et al. | 435/240.45 |
| 5,183,757 | 2/1993 | Roberts | 435/240.49 |
| 5,187,092 | 2/1993 | Uddin | 435/240.45 |
| 5,236,469 | 8/1993 | Carlson et al. | 47/57.6 |
| 5,294,549 | 3/1994 | Pullman | 435/240.45 |
| 5,413,930 | 5/1995 | Becwar et al. | 435/240.49 |
| 5,464,769 | 11/1995 | Attree et al. | 435/240.4 |
| 5,563,061 | 10/1996 | Gupta | 435/240.45 |
| 5,985,667 | 11/1999 | Attree et al. | 435/422 |

OTHER PUBLICATIONS

Bewley, J. D. and M. Black. *Physiology and Biochemistry of Seeds*, vol. 1, pp. 1–4, Springer–Verlag, Berlin (1978).
Carlson, William C. Lifting, storing, and transporting southern pine seedlings. In *Forest Regeneration Manual*, M. L. Duryes and P. M. Dougherty eds., pp. 291–301, Kluwer Academic Publischers, (1991).
Libby, W. J. Clonal Propagation. *Journal of Forestry* 84: 37–38, 42 (1986).
Mullin, R. E. Effects of root exposure on establishment and growth of outplanted trees. In Internationsl Symposium: Ecology and Physiology of Root Growth. pp. 229–242, Akademie–Verlag, Berlin (1974).
Bewley and Black, Physiology and Biochemistry of Seeds, vol. 1, p 2, Springer–Verlag, Berlin, Heidelberg, and New York, 1978.
Mullin, in II. International Symposium Ecology and Physiology of Root Growth, pp 229–242, Acadamie–Verlag, Berlin, 1974.
W.C. Carlson in Forest Regeneration Manual, pp. 291–301, Kluwer Academic Publishers, 1991.
W.J. Libby, in Journal of Forestry 84:37–38, 42, 1986.
Finch–Savage, Effects of cold storage of germinated vegetable seeds prior to fluid drilling on emergence and yield of field crops, Ann. appl. Biol. 97:345–352, 1981.
Grossnickle et al., Interior Spruce Seedlings Compared with Emblings Produced from Somatic Embryogenesis. I. Nursery development, fall acclimation, and over–winter storage, Can. J. For. Res., vol. 24: 1376–1384, 1994.

Lumis et al., Transplanting Method Influences Survival and Growth of Bare–Root Coniferous Nursery Stock, Journal of Arboriculture 6(10): 261–268, 1980.
Barnett, J. P., J. C. Brisette, and A. G. Kais. Improving field performance of southern pine seedlings by treating with fungicide before storage. *Southern Journal of Applied Forestry* 12(4): 281–285 (1998).
Brisette, J. C., J. P. Barnett, and J. P. Jones. Fungicides improve field performance of stored loblolly and longleaf pine seedlings. *Southern Journal of Applied Forestry* 20(1): 5–9 (1996).
Hinesley, L. E. Cold storage of Fraser fir seedlings. *Forest Science* 28(4): 772–776 (1982).
Lumis, Glen P. and A. G. Johnson. Transplanting method influences survival and growth of bare–root coniferous nursery stock. *Journal of Arboriculture* 6(10): 261–268 (1980).
Mason, W. L. and H. McKay. Evaluating the quality olf Sitka Spruce planting stock before and after cold storage. Combined Proceedings—International Plant Propagators Society 39:234–242 (1989).
McKay, H. M. and W. L. Mason Physiological indicators of tolerance to cold storage in Sitka spruce and Douglas–fir seedlings. *Canadian Journal of Forest Research* 21:890–901 (1991).
Struve, D. K. Bare root shade tree whip production in containers. *Journal of Environmental Horticulture* 14(1): 13–17 (1996).
Finch–Savage, W. The effects of cold storage of germinated vegetable seeds prior to fluid drilling on emergence and yield of field crops. *Annals of Applied Botany* 97:345–352 (1981).
Grossnickle, S. C., J.E. Major, and R. S. Folk. Interior spruce seedlings compared with emblings produced from somatic embryogenesis. I. Nursery development, fall acclimation, and over–winter storage. *Canadian Journal of Forestry Research* 24 (7): 1376–1384 (1994).
Frazier, D.C., S. C. West,and R. D. Wooton. Storage of pregerminated seed of snapdragon (*Antirrhinum majus* L.) in hydrophilic gels. *Journal of American Horticultural Science* 107(4):660–664 (1982).
Hempel, T. and M. Hempel. The influence of temperature, period and mode of storage of gerbera propagated in vitro on the quality of stored material. *Rosliny Ozbodne* Series B, 10:85–90 (1985).

(List continued on next page.)

*Primary Examiner*—David T. Fox
*Assistant Examiner*—Anne Marie Grunberg

[57] ABSTRACT

Germinants of conifer somatic embryos can be held for periods of up to several weeks in water in order to accumulate them for potting. Surprisingly, germinants held at temperatures near freezing showed superior survival after potting and twenty weeks greenhouse growth when compared to those potted immediately after removal from the germination medium. It was also found useful to store the germinants in a high humidity environment or even on the germination medium under cold conditions.

13 Claims, No Drawings

OTHER PUBLICATIONS

Knowles, N. R, and W. W. Dun. Effects of cultivar and storage duration on emergence and yield of fluid drilled pre-germinated lettuce seed. *Scientia Horticulturae* 31:25–33 (1987).

Roberts, D. R., B. C. S. Sutton, and B. S. Flinn. Synchronous and high frequency germination of interior spruce somatic embryos following partial drying at high relative humidity. *Canadian Journal of Botany* 68:1086–1090 (1990).

Roberts, D.R., W. R. Lazaroff, and F. B. Webster. Interaction between maturation and high relative humidity treatments and their effects on germination of sitka spruce somatic embryos. *Journal of Plant Physiology* 138:1–6 (1991).

Roberts, D. R., F. B. Webster, B. S. Flinn, W. R. Lazaroff, and D. R. Cyr. Somatic embryogenesis of spruce. InSynseeds: *Applications of Synthetic Seeds to Crop Improvement*, Keith Redenbaugh ed. CRC press, Ann Arbor (1993).

Wurr, D. C. E., R. J. Darby, and J. R. Fellows. The effect of cold storing pregeminated lettuce seeds on radicle development and seedling emergence. *Annals of Applied Botany* 97:335–343 (1981).

METHOD FOR STORING AND IMPROVING THE SURVIVAL RATE OF CONIFER SOMATIC EMBRYO GERMINANTS

This application claims priority from provisional application Ser. No. 60/066,897, filed Nov. 20, 1997.

BACKGROUND OF THE INVENTION

Propagation of commercially important tree species for reforestation of managed forests has assumed great importance as the urban expansion and the demand for wood increases while world forests continue to disappear at an alarming rate. Tree nurseries now supply seedlings in the tens of millions annually. Most of these seedlings are grown from seed produced in seed orchards stocked with genetically selected trees. However, full genetic gain is usually not realized since most orchards are open pollinated; i.e. by wild pollen of unknown origin and genetic quality. A very small amount of full sib seed is produced in which both cone and pollen parents are controlled. However, this seed is very expensive since its production is extremely labor intensive. Immature female strobili must be covered with bags to prevent entry of wild pollen. Selected pollen is then injected into the bags at the time when the female strobili are most receptive to fertilization. Little of this full sib seed ever finds its way directly into the forest as nursery seedlings because of the high cost. Much is used in nurseries as stock for producing rooted cuttings. Others is dedicated for progeny trials for selection of stock for future generation seed orchards.

Tissue culture is one method by which plants of known genetic characteristics have been produced for many years. Originally this procedure was carried out only on ornamental species. Various orchid varieties and Boston fern might be cited as examples. Extensive research on conifers came later, in part because they were far more intractable. The earliest successful procedures with conifers were based on organogenesis. Portions of a newly sprouted seedling were placed on a bud-inducing medium. The buds were then separated and placed on other media for further propagation and root development. Two problems prevented wide use. The process was highly labor intensive and genetic mutation was common.

Clonal propagation of forest species by embryogenesis appeared to be a more promising route, although the technical obstacles have been severe. The first successful embryogenesis of a conifer was not achieved until about 1975. For the decade thereafter the number of tissue culture propagated embryos that were successfully converted into growing trees was probably no more than a few dozen. A large body of related literature now exists including a significant number of patents. As exemplary United States patents the following might be cited: Gupta et al. U.S. Pat. No. 5,036,007; Roberts U.S. Pat. No. 5,183,757; Uddin U.S. Pat. No. 5,187,092; Pullman et al. U.S. Pat. No. 5,294,549; Becwar et al. U.S. Pat. No. 5,413,930 Attree et al. U.S. Pat. No. 5,464,769; and Gupta U.S. Pat. No. 5,563,061. These patents deal primarily with the propagation of Douglas-fir (*Pseudotsuga menziesii* (Mirb.) Franco), loblolly pine (*Pinus taeda* L.) and various spruce (*Picea*) species. The procedures share many features in common. An explant, often an immature seed or the embryo from an immature seed, is placed on a gelled initiation medium. This medium usually will contain plant growth hormones from the groups known as auxins and cytokinins. If initiation is successful a gelatinous mass containing multiple immature embryos will be generated in several weeks. This mass is then removed and subcultured on a maintenance and multiplication medium which may be gelled, liquid, or some combination of these. The maintenance medium will typically have a reduced concentration of plant growth hormones. Subcultures to fresh medium are required on a regular basis. While the clone is on the maintenance medium, embryo size growth is limited. Embryos from maintenance may then be placed on a development medium. This normally lacks the auxins and cytokinins but may instead include the hormone abscisic acid. Here somatic embryos develop into cotyledonary embryos with a size and morphology that closely resembles their mature zygotic counterparts. A further treatment following development may be a partial desiccation after which the embryos are placed on a hormone free germination medium. During the next several weeks radicle and epicotyl elongation will occur. The germinants or emblings are then removed and placed in soil for further development into plantlets. After a period of greenhouse growth they may then be outplanted. Alternatively, the embryos removed from the development medium may be placed in manufactured seeds; e.g., as shown in Carlson et al. U.S. Pat. No. 5,236,469.

Even though great progress has been made in conifer tissue culture in the past two decades it is only now beginning to be of commercial significance as a source of reforestation stock. For some species and for particular clones of any species, propagation by tissue culture has been far less successful than desired. Significant biological and engineering problems remain. One problem has been that conversion percentage from somatic embryos to plants growing in soil has frequently been lower than desired. Often as low as 10% of the transplanted germinants will survive and 40% survival has been considered good. It is interesting that this survival percentage also holds for excised zygotic embryos. A further problem is logistical rather than biological. Unless the conifer somatic embryos are to be processed into manufactured seeds, they are presently individually removed from the sterile development medium by hand and placed on a germination medium. After an appropriate time those embryos that germinate are placed in a potting soil mixture for further growth. While this poses no problem on a laboratory scale it does for automation on a production basis when many hundreds of thousands of plants may be wanted. A method has been needed to accumulate germinants that may have become available over a period of days or weeks so that potting might be done within a relatively short time interval.

It is known that certain vegetable seeds may be pregerminated and stored in aerated water or at high humidity at temperatures of 0° C. to 4° C. for several days and then planted without loss of viability. As examples see Finch-Savage, *Annals of Applied Biology* 97: 345–352 (1981) or Wurr et al., pp 335–343 of the same journal. Similar treatment has also been used on ornamentals such as snapdragon; e.g., Frazier et al., *Journal of the American Society of Horticultural Science*, 107 (4): 660–664 (1982). In all of these cases pregermination was apparently allowed to proceed only to the point of radicle emergence prior to the wet cold storage treatment. Gerbera daisy embryos produced by tissue culture and rooted have been stored cold on filter paper in closed boxes. Moisture conditions were not clearly specified; e.g., Hempel et al., *Rośliny Ozdobne* Series B, 10: 85–90 (1985). To the present applicant's knowledge similar techniques have not been tried with conifer somatic embryo germinants or on any plants in which a well developed epicotyl has already been formed.

The present invention addresses the problem of accumulation and storage of any desired quantity of conifer somatic embryo germinants without loss of vigor until they can be conveniently and efficiently planted. The method further significantly improves longer term conversion success from germinants to plants ready to set out in the forest.

SUMMARY OF THE INVENTION

The present invention is directed to a method whereby conifer somatic embryo germinants may be accumulated and stored without loss of vigor until such time as it is convenient to transfer them into a potting medium. By "germinant" or "embling" is here meant an immature plant that possesses a well defined epicotyl and radicle, both readily apparent to the naked eye. The germinants are produced by first culturing conifer somatic embryos by known protocols. After the embryos have reached a mature cotyledonary stage they are then placed individually on a germination medium for a sufficient period of time for an epicotyl and radicle to develop. This time period may range between 4 and 14 weeks, depending on the particular species and genotype. More typically it is between 8 and 12 weeks. The germinants, which typically may have an epicotyl of about 10 mm or somewhat greater, are removed and immediately placed with the radicle in water to ensure good wetting. They may then be accumulated and stored for a period of time until it is convenient to plant them in a potting medium as transplants for further greenhouse growth.

Surprisingly, by keeping the germinants in water for a period greater than one hour, preferably at least one day, at a temperature no greater than room ambient conditions up to a maximum of about 24° C., long term survival rate is not significantly reduced for periods up to two or three days. At lower storage temperatures, long term survival rate appears to be significantly enhanced and the permissible holding period significantly extended. A preferred temperature is below 10° C. and most preferably the temperature is held in a range of 1° C. to 5° C. This improvement in survival rate is entirely unexpected since the germinants are very tender and in an active growing condition. Placing them in a cold environment as low as 1° C. to 5° C. and removing them from a nutrient source would normally be expected to induce significant stress leading to mortality.

The germinants may be retained in water at a suitable temperature for as long as the survival rate is not significantly reduced when transplanted into potting medium. Survival rate is here compared with that of germinants planted directly into the potting medium or after holding them in water at ambient room temperature for less than one hour. An optimum time for improving long term survival rate is 1–2 weeks at a temperature between 1° C. and 5° C. Much longer retention times have not been deleterious to most genotypes although deterioration usually begins to occur after about seven weeks.

It has not been found to be critical whether the germinants in water are stored in light or under dark conditions.

The method has been found to be equally suitable for both Douglas-fir and loblolly pine, the two most important United States timber species.

It is an object of the invention to provide a method whereby somatic embryo germinants may be retained in storage for considerable periods of time without deterioration.

It is another object to provide a method of somatic embryo germinant storage until it is convenient to transplant the germinants into potting medium or soil.

It is a further object to provide a method whereby the long term survival rate of somatic embryo germinants transplanted into soil is enhanced.

These and many other objects will become readily apparent upon reading the following detailed description of the invention.

DETAILED DESCRIPTION OF THE PREFERRED EMBODIMENTS

Embryos from five clones of Douglas-fir were grown similar to methods described in Gupta, U.S. Pat. No. 5,563, 061. The mature cotyledonary embryos were stratified by holding them while still on the development medium at 4° C. for four weeks. These were then placed on an agar gelled germination medium in petri dishes for 4–12 weeks until good epicotyl development was apparent. The germinants were removed individually from the germination medium when epicotyl stem length was generally about 10 mm. They were then placed in room temperature deionized water for transport from the laboratory to the greenhouse. A first control batch of germinants from each clone was potted immediately. Other batches were kept in water in sealed dishes under the conditions outlined in the tables below. No attempt was made to maintain sterility after removal from the germination medium. The potting medium consisted of equal parts of peat, vermiculite, and perlite. Sample size was about 30 germinants under each condition tested. The potted germinants were held for further growth in a greenhouse maintained at 24° C. for a 16 hour light period and at 18° C. for an 8 hour dark period. After 20 weeks the plants were rated for survival percentage.

EXAMPLE 1

Douglas-fir germinants of genotype A were treated as shown in the following table:

| Time in Water | Water Temperature | Lighting Conditions | Survival Percentage |
| --- | --- | --- | --- |
| <1 hour | Ambient | Light | 37% |
| 1 day | 4° C. | Dark | 52% |
| 3 days | 4° C. | Dark | 40% |
| 7 days | 4° C. | Dark | 48% |
| 1 day | 23° C. | 16 Light/8 Dark | 38% |
| 3 days | 23° C. | 16 Light/8 Dark | 26% |
| 3 days then | 4° C. | Dark | 38% |
| 4 days | 23° C. | 16 Light/8 Dark | |

It is readily evident that cold treatment in water has significantly increased 20 week survival percentage for this genotype. Prolonged treatment at ambient room temperature may not be detrimental but does not achieve noticeable improvement.

EXAMPLE 2

Douglas-fir germinants of genotype B failed to survive for 20 weeks under any conditions of treatment.

EXAMPLE 3

Douglas-fir germinants of genotype C were treated as shown in the fol- lowing table:

| Time in Water | Water Temperature | Lighting Conditions | Survival Percentage |
| --- | --- | --- | --- |
| <1 hour | Ambient | Light | 18% |
| 3 days | 4° C. | Dark | 37% |
| 7 days | 4° | Dark | 20% |

While there were beneficial results from the cold dark treatment in water under one condition, the results are equivocal and the experiment should be repeated.

EXAMPLE 4

Douglas-fir germinants of genotype D were treated as shown in the following table:

| Time in Water | Water Temperature | Lighting Conditions | Survival Percentage |
| --- | --- | --- | --- |
| <1 hour | Ambient | Light | 12% |
| 7 days | 4° C. | Dark | 40% |
| 14 days | 4° C. | Dark | 46% |

The 20 week survival benefits of the cold dark treatment in water are very dramatic for this genotype.

EXAMPLE 5

Douglas-fir germinants of genotype A were treated again as shown in the following table:

| Time in Water | Water Temperature | Lighting Conditions | Survival Percentage |
| --- | --- | --- | --- |
| <1 hour | Ambient | Light | 35% |
| 7 days | 4° C. | Dark | 68% |

Again, as for genotype D, the results for the cold dark treatment in water are dramatic with the 20 week survival rate nearly doubling.

The reason for the improvement in survival percentage is not well understood and was unexpected. The prolonged soak may possibly serve to rehydrate water stressed germinants. It could be reducing the load of undesirable constituents of previous tissue culture media which can have negative carryover effects on the next stage of plant development.

EXAMPLE 6

Douglas-fir germinants of five additional genotypes known to have very high survival rates were treated as described above by placing the germinants in deionized water and stored in the dark at a temperature of 4° C. for varying time periods. Survival percentages after 12 weeks are given in the following table.

| Storage Time | Genotype F | Genotype G | Genotype H | Genotype I | Genotype J |
| --- | --- | --- | --- | --- | --- |
| Non-stored | 87% | 77% | 88% | 82% | 97% |
| 2–4 days | — | 74% | 91% | — | —% |
| 1 week | 90% | 86% | 93% | 88% | 100% |
| 2 weeks | 97% | 75% | 87%* | 88% | 97% |
| 4 weeks | 93% | 79% | 94%** | 88% | 90% |
| 7 weeks | 53% | 48% | 58% | — | — |
| 10 weeks | 7% | 52% | 13% | — | — |
| 14 weeks | 27% | 10% | 4% | — | — |

*3 week storage
**5 week storage

It is readily apparent that storage out to four weeks has little or no adverse effect on germination percentage for the five genotypes used in this test. After seven weeks the effect was genotype dependent but deterioration was beginning to be generally noticed. The initial germination percentage was high for all genotypes but was improved by the cold treatment in water in all cases after one week of treatment.

EXAMPLE 7

Germinants of three additional Douglas-fir genotypes known to germinate well were placed in deionized water for one week under varying light and temperature conditions. Temperatures were ambient, about 23° C. and about 4° C. Survival percentages at twelve weeks are given below.

| Storage Environment | Genotype K | Genotype L | Genotype M |
| --- | --- | --- | --- |
| Non-stored | — | 75% | 70% |
| Cold-Dark | 91% | 83% | 83% |
| Cold-Light | 97% | 80% | 83% |
| Warm-Dark | 76% | 57% | 57% |
| Warm-Light | 88% | 57% | 73% |

For the time period studied the cold storage treatment proved to be clearly superior to the warm storage. The effect of light vs dark environment was less. pronounced and the value of one over the other varied by genotype.

EXAMPLE 8

To determine whether actual contact with water was essential an experiment was made to see whether a high humidity environment was as suitable as water immersion. Douglas-fir germinants were placed either in water or wrapped in wet filter paper and stored at about 4° C. for varying time periods. Greenhouse survival was monitored to determine any effects. Results showing survival at 12 weeks are given in the table below.

| Storage Time | Soak | | Wrap | |
| --- | --- | --- | --- | --- |
| | Genotype J | Genotype N | Genotype J | Genotype N |
| Non-stored | 97% | 81% | 97% | 81% |
| 1 week | 100% | 94% | 90% | 93% |
| 2 weeks | 97% | 87% | 87% | 79% |
| 4 weeks | 90% | — | 67% | — |

While results of storage at one week are somewhat equivocal, for longer periods storage directly in water is superior to the high humidity wrap. However, for shorter periods, high humidity storage is an acceptable procedure.

Relative humidity should be greater than 90%, preferably greater than 98%.

EXAMPLE 9

A test was made to compare water storage with storage while still on germination medium. Conditions were dark at about 4° C. for one or two weeks. Survival percentages at 12 weeks are seen below.

| Storage Method | Genotype O | Genotype P | Genotype Q |
|---|---|---|---|
| Non-stored | — | — | 90% |
| Water, 1 week | 80% | 95% | — |
| Germ. Med., 1 week | 68% | 96% | 85% |
| Germ. Med., 2 weeks | — | — | 73% |

Storage on germination medium for up to two weeks does not appear to be seriously deleterious although storage in water appears to be a superior treatment.

EXAMPLE 10

Loblolly pine somatic embryo germinants of two genotypes were tested for wet response at 4° C. Survival percentages after 12 weeks storage are as given below:

| | Percent Survival | |
|---|---|---|
| Time in Storage | Genotype 7 | Genotype 8 |
| Control (overnight) | 75% | 28% |
| 2 days | 72% | — |
| 3 days | 74% | — |
| 7 days | 62% | 85% |

Response of loblolly pine is similar to Douglas-fir. The increased survival of Genotype 8 is striking.

Applicant has herein disclosed the best mode known of practicing her invention. It will be evident that many changes could be made from those examples described without departing from the spirit of the invention. The invention should thus be considered as limited only as it is defined in the following claims.

What is claimed is:

1. A method of storing conifer somatic embryo germinants germinated on a germination medium for delayed transplanting into a growing medium which comprises:
    removing the germinants from the germination medium said germinants comprising a visible, well-defined epicotyl and radicle;
    placing the germinants in water for a time greater than about 1 hour at a temperature below about 24° C.; and
    removing the germinants from the water and transplanting them into a potting medium for further growth.

2. The method of claim 1 in which the water temperature is in the range of about 1° C. to about 10° C.

3. The method of claim 1 in which the water temperature is in the range of about 1° C. to about 5° C.

4. The method of claim 1 or 2 in which the germinants are retained in the water for a period of at least about 1 day.

5. The method of claim 4 in which the germinants are retained in the water for a period between about 1 day and 7 weeks.

6. The method of claim 1 in which the germinants in water are stored under dark conditions.

7. The method of claim 1 in which the germinants in water are stored under light.

8. The method of claim 1 in which the germinants are Douglas-fir.

9. The method of claim 1 in which the germinants are loblolly pine.

10. A method of storing conifer somatic embryo germinants germinated on a germination medium for delayed transplanting into a growing medium which comprises:
    removing the germinants from the germination medium, said germinants comprising a visible well-defined epicotyl and radicle;
    placing and retaining the germinants in an environment in which relative humidity is greater than 90%; and
    removing the germinants from the high humidity environment and transplanting them into a potting medium for further growth.

11. The method of claim 10 in which the relative humidity in which the germinants are placed is equal to or greater than 98%.

12. A method of storing conifer somatic embryo germinants germinated on a germination medium for delayed transplanting into a growing medium which comprises:
    placing the germinants while still on the germination medium in a cold environment in which the temperature is in the range of 1°–5° C. for a time period up to two weeks, said germinants comprising a visible, well-defined epicotyl and radicle; and
    removing the germinants from the cold environment and transplanting them into a potting medium for further growth.

13. The method of claim 1 in which the germinants are removed from the water before the time at which the survival rate is reduced when compared with the survival rate of germinants not treated in water or treated in water less than one hour at ambient room temperature.

* * * * *